(12) United States Patent
Brostmeyer et al.

(10) Patent No.: US 7,174,797 B2
(45) Date of Patent: Feb. 13, 2007

(54) HIGH TEMPERATURE AND PRESSURE TESTING FACILITY

(75) Inventors: Joseph Brostmeyer, Jupiter, FL (US); Jack Wilson, Palm Beach, FL (US); Todd A. Ebert, West Palm Beach, FL (US)

(73) Assignee: Florida Turbine Technologies, Inc., Jupiter, FL (US)

( * ) Notice: Subject to any disclaimer, the term of this patent is extended or adjusted under 35 U.S.C. 154(b) by 148 days.

(21) Appl. No.: 10/685,339

(22) Filed: Oct. 14, 2003

(65) Prior Publication Data

US 2004/0216535 A1    Nov. 4, 2004

Related U.S. Application Data

(60) Provisional application No. 60/482,560, filed on Jun. 25, 2003, provisional application No. 60/418,549, filed on Oct. 15, 2002.

(51) Int. Cl.
*G01N 33/00*    (2006.01)

(52) U.S. Cl. ........................ 73/865.6; 73/866
(58) Field of Classification Search ............... 73/865.6, 73/150 R, 866
See application file for complete search history.

(56) References Cited

U.S. PATENT DOCUMENTS

| | | | |
|---|---|---|---|
| 3,029,635 A * | 4/1962 | Fetz | 73/147 |
| 3,263,485 A | 8/1966 | Mahmoodi | |
| 3,323,586 A * | 6/1967 | Burne et al. | 165/154 |
| 3,886,791 A * | 6/1975 | Grossman | 73/150 R |
| 5,260,218 A | 11/1993 | Garde | |
| 5,707,147 A | 1/1998 | Kurkowski et al. | |
| 5,720,554 A * | 2/1998 | Smith et al. | 374/1 |

FOREIGN PATENT DOCUMENTS

| | | | |
|---|---|---|---|
| EP | 1136780 A | * | 9/2001 |
| JP | 2003315253 A | * | 11/2003 |

* cited by examiner

*Primary Examiner*—Hezron Williams
*Assistant Examiner*—Nashmiya Fayyaz
(74) *Attorney, Agent, or Firm*—Christopher & Weisberg, P.A.

(57) ABSTRACT

A test facility is provided for testing materials under high temperature, pressure, and mechanical loads. The facility provides a physically scaled system that simulates conditions in hot sections of gas turbine engines. A test article is coated with a test material and exposed to a hot combusting flow in a test section housing. The article may be a pipe or conduit member oriented at any direction to the flow. A second cooler flow of fluid is channeled through the test article to create a sharp temperature gradient in the test article and through the test material. A liquid-cooled sleeve is disposed about the test article to create an annular channel of combusting flow over the test article. The downstream end of the second cooler flow is connected to the upstream end of the main hot flow at the combustion chamber.

7 Claims, 5 Drawing Sheets

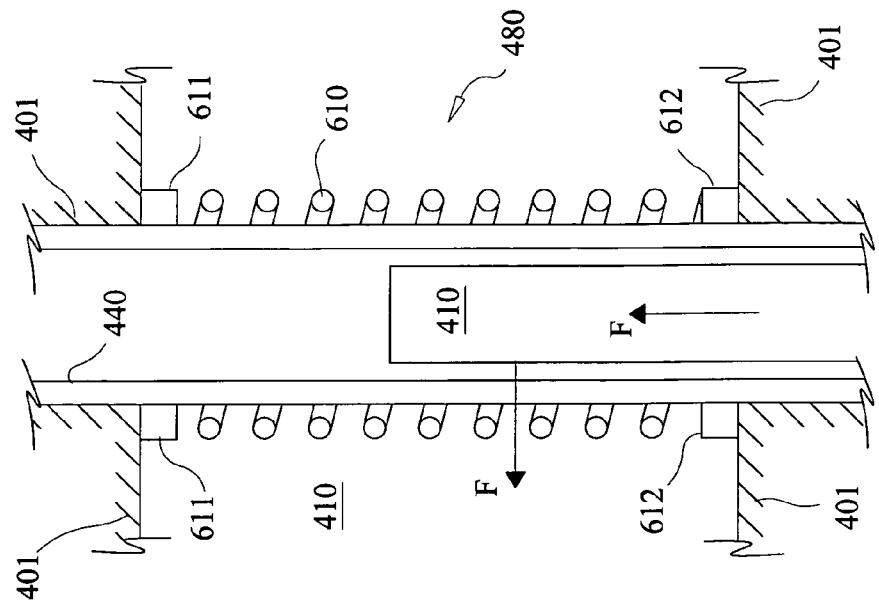
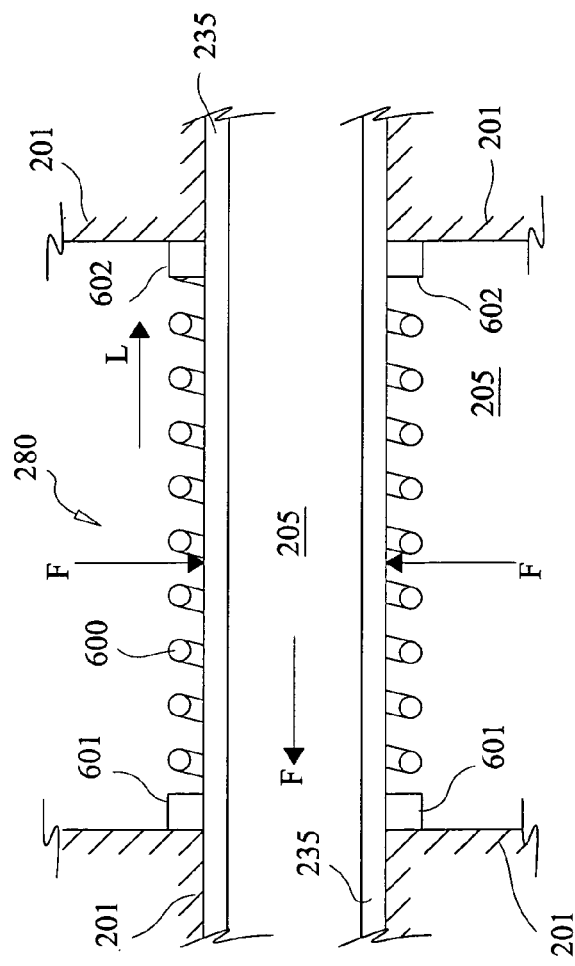
FIG. 6B
FIG. 6A

HIGH TEMPERATURE AND PRESSURE TESTING FACILITY

CROSS-REFERENCE TO RELATED APPLICATION

This application is related to and claims priority to U.S. Provisional Patent Application Ser. No. 60/418,549, filed Oct. 15, 2002, entitled HIGH TEMPERATURE AND PRESSURE TESTING FACILITY, and U.S. Provisional Patent Application Ser. No. 60/482,560, filed Jun. 25, 2003, entitled HIGH TEMPERATURE AND PRESSURE TESTING FACILITY, the entirety of which is incorporated herein by reference.

STATEMENT REGARDING FEDERALLY SPONSORED RESEARCH OR DEVELOPMENT n/a

FIELD OF THE INVENTION

The present invention relates to a system and method for testing materials in high temperature and pressure environments, thereby simulating the conditions in a gas turbine engine.

BACKGROUND OF THE INVENTION

Testing of advanced components, materials, and coatings under extreme conditions that directly simulate engine operation is very costly. In most cases it involves the installation of the test article(s) in a special test engine in the case of aircraft engines, or in an operating gas turbine in the case of industrial gas turbines.

Use of a special test engine is extremely expensive. The cost of operating a test aircraft engine can run as high as $10,000 per operating hour. Since the test article must be tested for thousands of hours to meet flight certification, full life engine testing must be reserved for final testing of hardware for qualification. Therefore a low-cost testing facility is needed that can test this hardware during the experimental, high risk phase of development, and where failure to the test article does not have the potential to cause significant and costly damage to the test facility.

For industrial gas turbines, an existing operating gas turbine may be used. However, even this approach results in high costs due to uncertainty of the test article's performance, life, and potential for destructive failure, and the resulting impact on power plant's repairs, operability, and availability.

Existing testing facilities for testing hot section material systems are generally categorized as "burner rigs". They typically use hot flame impingement onto the test article(s) to ascertain material/coating durability under hot conditions. While these burner tests are more easily accomplished than full engine testing they exclude some of the effects that induce material and/or coating failures like thermal mechanical failure in the base metal, coating spallation due to high thermal gradients, erosion due to high velocity flow, corrosion degradation due to trace elements in fuel at operating temperatures and pressures, ability to apply mechanical loads, and radiation loads in the combustor. It is desirable therefore to provide a test facility that effectively subjects test articles and materials to high heat and mechanical loads, high thermal gradients, high flow velocity environments, and other conditions exemplary of gas turbine engines. Furthermore, the test facility must be sufficiently scaled to meet cost and operability requirements.

There are additional testing problems associated with testing hardware intended for advanced engines that are yet to be developed. In this case, existing engines cannot provide the operating temperatures and pressures that this hardware will endure in the advanced engine. Again, a test facility that can provide these test conditions at low cost would greatly increase design confidence while reducing the life cycle cost for advanced engine development.

SUMMARY OF THE INVENTION

The present invention advantageously provides a test facility for testing a material. The facility includes a test section housing defining a first flow path and a second flow path, each flow path having upstream and downstream ends, respectively. The facility further includes a conduit enclosing a portion of the first flow path for accommodation therethrough of a first fluid flow having a first temperature, and a sleeve concentric about the conduit to define an annular portion of the second flow path for accommodation therethrough of a second fluid flow having a temperature higher than the first temperature. A test material is disposed on the conduit in contact with the annular portion.

In another embodiment of the present invention, a test facility is provided for testing a material, having a test section housing defining a primary flow path for accommodation therethrough of a first fluid flow having a first temperature. At least one test article encloses a portion of at least one secondary flow path for accommodation therethrough of a fluid flow having a temperature lower than the first temperature. A test material is disposed on an outer surface of the at least one test article in contact with the primary flow path.

In still another embodiment, the present invention provides a gas turbine engine simulation system. The system includes a test section housing having a first flow pathway for the flow of hot combusting fluid, a supply means for providing compressed fluid to the test section, and a combustion means for combusting the compressed fluid in the first flow pathway. A test article is disposed in the test section housing having a test material deposited on an outer surface of the test article, in contact with a portion of the first flow pathway. A first cooling means is incorporated with the test article for providing a temperature gradient through the test article.

Yet another embodiment of the present invention provides a method for testing a material under high temperature and pressure. A compressed fluid is supplied to a test section having a first flow pathway. A portion of the compressed fluid is directed through a second flow pathway defined in a test article disposed in the test section in a portion of the first flow pathway. Fuel is combusted with the compressed fluid to provide a high temperature and pressure fluid flow through the portion of the first flow pathway. A cooling fluid flow is provided through the second flow pathway to create a temperature gradient in the test article.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 5 is a perspective view of a longitudinal cross-section of the embodiment shown in FIG. 4; and FIGS. 6A and 6B show alternate embodiments of a spring-loaded compression seal incorporated into the present invention.

DETAILED DESCRIPTION OF THE INVENTION

As used herein, the term "high temperature and pressure" shall generally refer to those temperatures and pressures commonly found in gas turbine or other engine components, including, but not limited to, axial and centrifugal compressors, combustor sections, turbine sections, diffusers, nozzles, or any other component of turbomachinery or other engines. Also as used herein, the term "test material" shall refer to one or a number of different substances, elements, compounds, or mixtures thereof, including a variety of thermal barrier coating (TBC) materials, or any other material in solid, semi-solid, or fluid form.

Also as used herein, a "facility" shall mean any device or arrangement of devices or systems, including individual components and aggregation of components. As used herein, a "conduit" shall mean any object having a path therethrough for the passage of a fluid. A path, which may also be referred to as a flow path or pathway, may be straight or curved, regular or irregular, and may include several independent passages from one point to another.

Figure 1:
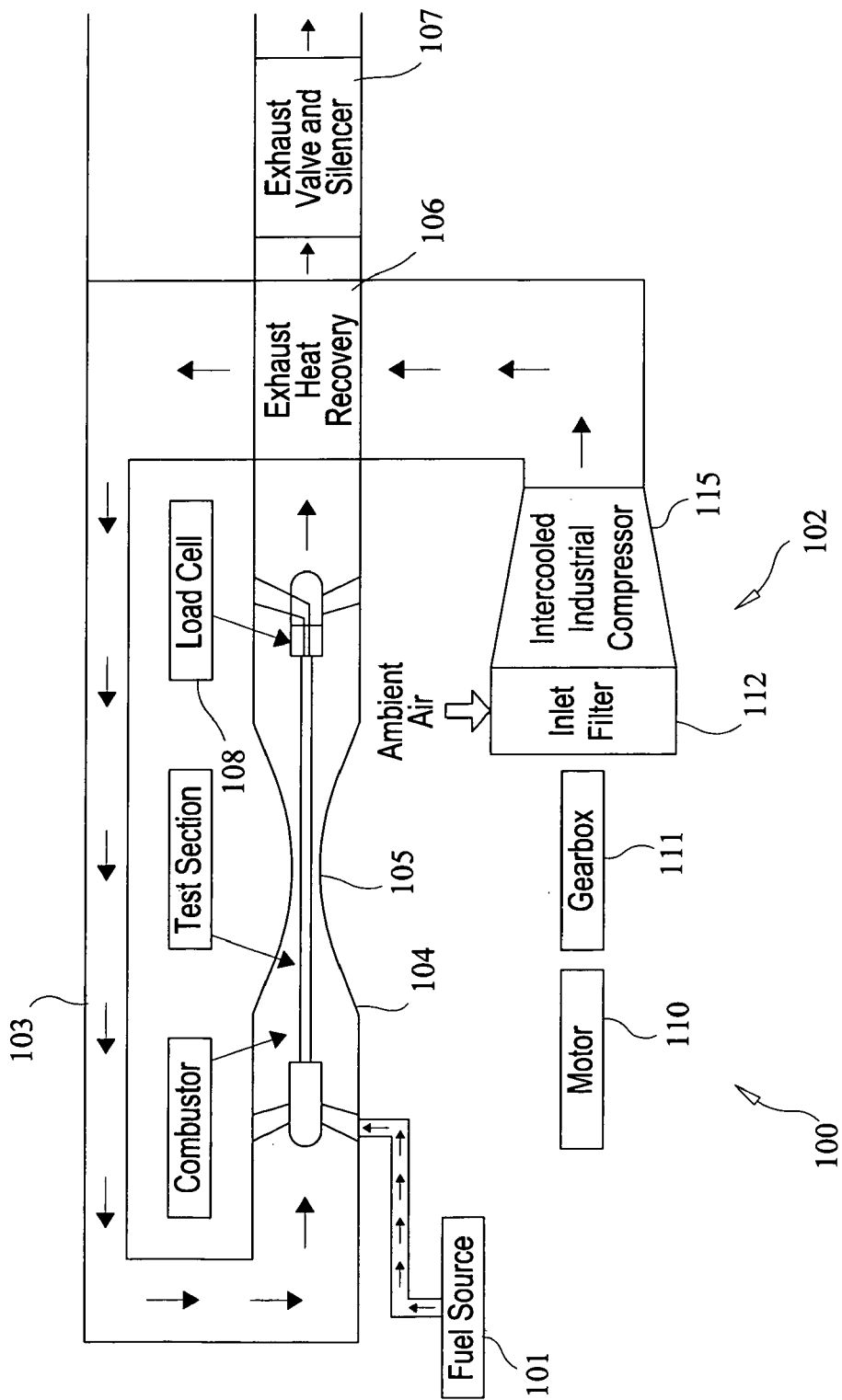
FIG. 1 is a schematic of the test facility system of the present invention.

Turning now to the drawing figures, FIG. 1 is a schematic of a test facility system arranged in accordance with the principles of the present invention. The test facility 100 includes a fuel source 101, and air source 102, a series of conduits 103 for carrying the compressed air from the air source 102 to a combustor section 104. A test section 105 may be incorporated into the combustor section 104, where the two components may form a single device. Alternatively, the combustor section 104 may be separate and distinguishable from the test section, or may be detachable or removable therefrom. A heat exchanger such as an exhaust heat recovery unit 106 may be coupled downstream of the test section. The heat recovery unit 106 may therefore be in thermal communication with the source of compressed fluid from the source 102. An exhaust valve and silencer unit 107 may be coupled downstream of the exhaust heat recovery unit 106, or directly downstream of the test section 105. A load cell 108 may be incorporated into the test section 105 to provide mechanical loads to a test specimen or article lodged in the test section 105.

The air source 102 may also include several components, including a motor 110, a gearbox 111, an inlet filter 112, and an industrial compressor 115. Ambient air is drawn in through the filter 112 to the compressor 115. The motor 110 and gearbox 111 drive the compressor 115, which outputs compressed air into the conduits 103 for delivery to the test section 105. However, the present invention may use not only air as a fluid source, but any fluid, in gaseous or liquid form, as a source of compressed fluid which may be combusted and or mixed with fuel from the fuel source 101 in the combustor section 104.

As illustrated in FIG. 1, the present invention provides an open system that uses only enough working fluid flow to achieve sufficient hardware scale to lower testing costs. Controlled metric testing may be used to isolate critical empirical factors while testing across the full range of conditions to which hardware will be exposed in a real engine. The working fluid is provided by the source 102, where it is compressed by the compressor 115. The compressor 115 may use intercooling to compress the air to a high pressure (such as 800 psia). Such a high pressure compressor may be either of the reciprocating or high speed centrifugal design. The compressed air is then routed through conduits 103 to the combustor section 104 and test section 105. The entire system may be arranged at a lower physical scale than that of a typical engine, but with enough of a flow to create an effective environment to test materials therein. By way of non-limiting example, exemplary flow rates through test section 105 range from 0.25 lb/sec to 1.0 lb/sec.

The air exiting the compressor 115 may then be preheated in the exhaust recovery heat exchanger 106 (typically to a value of 1000° F. up to 1300° F.) prior to being sent into the combustor. However, such a preheating element is not necessary. Fuel such as natural gas or jet fuel is pumped to a pressure higher than that of the air to allow for proper distribution in the combustor 104 via fuel injection nozzles (not shown), where it is combusted to achieve very high combustor exit temperatures. A typical example of exit temperatures may be the stoichiometric limit for hydrocarbon fuels, which will result in a temperature of approximately 4000–4500° F.

Test articles or materials may be inserted into any portion of the flow in the test section 105, from the inlet to the exit. Or, the test articles or materials, along with any instrumentation probes may be inserted into the combustion chamber 104. The test facility 100 is thereby able to apply both convection and thermal radiation loads on the test article(s) inserted into the combustion chamber 104. Furthermore, the flame generated in the combustion chamber 104 may propagate into the test section 105, such that thermal loads, including conduction, convection, and radiation loads, as well as erosive, fluid dynamic, mechanical, or other stresses and loads may be applied to the test article as desired.

After combustion, the flow is accelerated into the test section 105 of the facility, which, in a first embodiment of the present invention, may include a cooled inner conduit or pipe within an outer pipe or sleeve. The inner pipe may have test material coupons or coatings (not shown) deposited or fixed on its outer surface, which may be loaded using the load cell 108 to evaluate both steady-state and transient loads (such as vibration or pull loads). Realistic thermal gradients through the test samples are accomplished in the test section 105 by simulating engine hot gas path conditions on one side of the inner pipe, and cooling side heat transfer on the other side. The test article may also be film cooled if desired. The load cell 108 controls are located outside the test section 105 housing. For each of the combustor 104, test section 105, and high temperature downstream parts, a combination of convective and film cooling is used to maintain material operating temperatures within acceptable limits. As shown below in FIGS. 2 and 3, the test section 105 housing includes a thermal barrier coating lined metallic sleeve, possibly of copper, with channels used as axial water jackets for advective cooling combined with latent heat via subcooled forced convection boiling.

Figure 2:
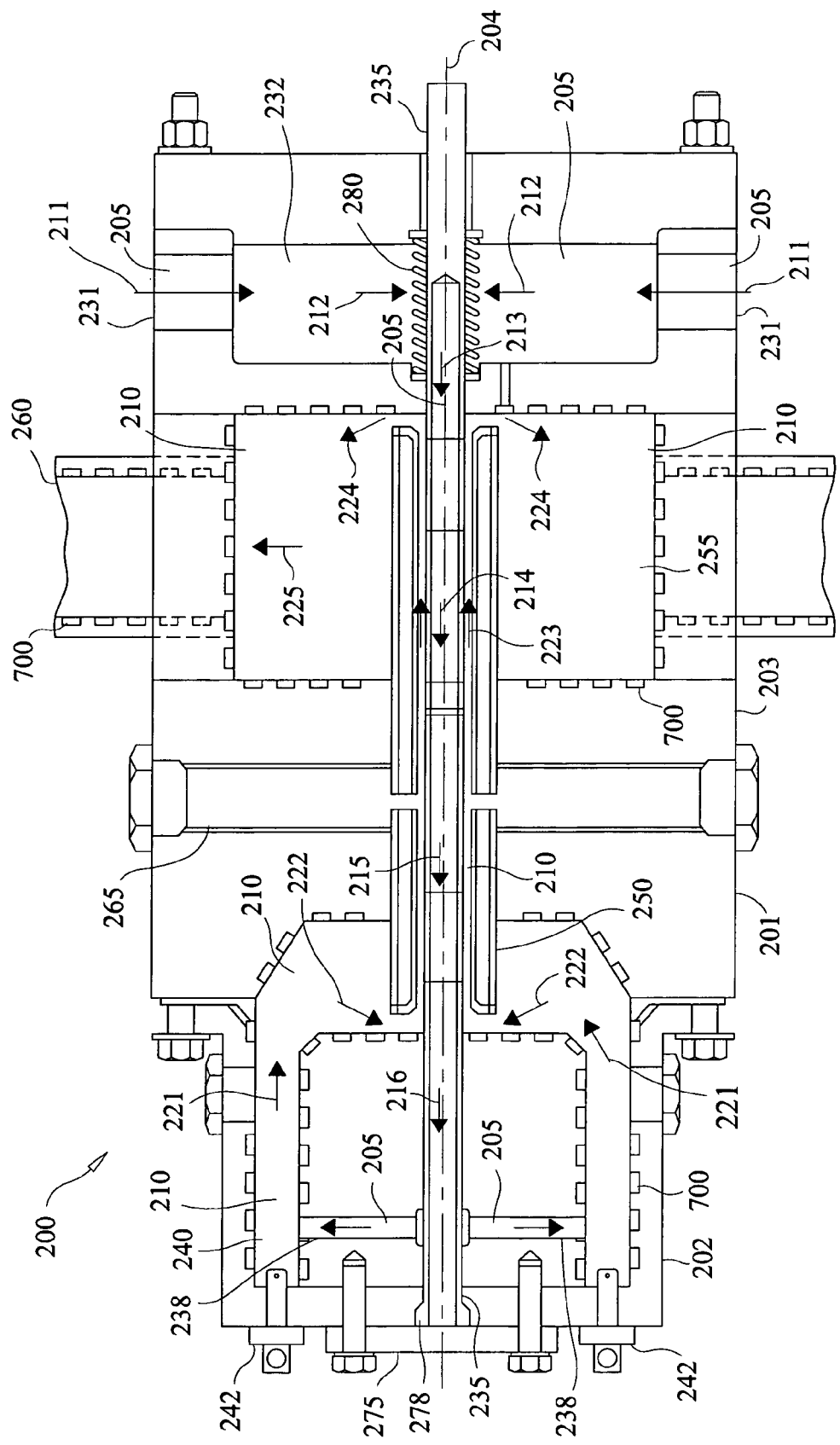
FIG. 2 is a longitudinal cross-sectional view of a first embodiment of the test section incorporated into the test facility of the present invention.
Figure 4:
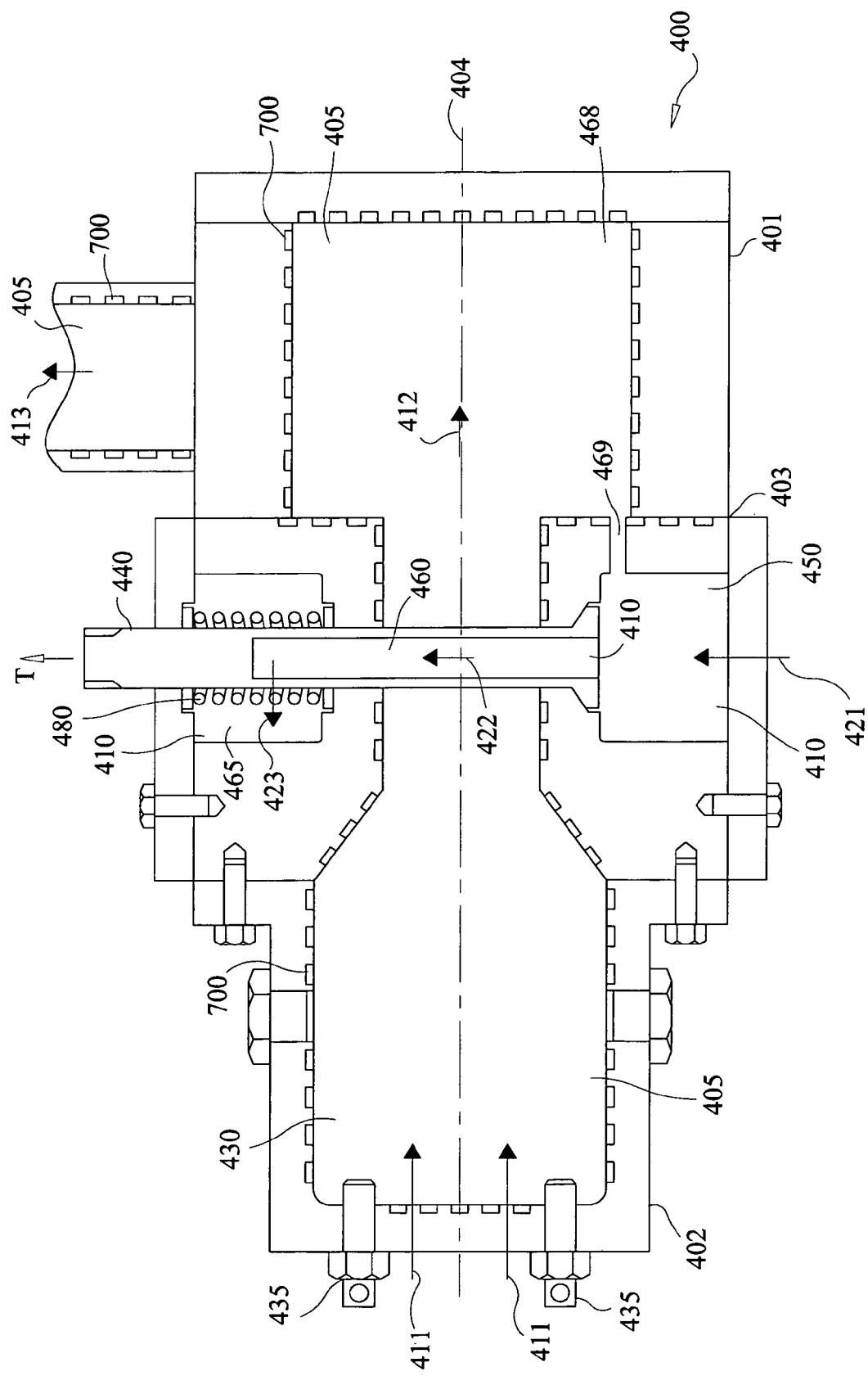
FIG. 4 is a longitudinal cross-sectional view of a second embodiment of the test section incorporated into the test facility of the present invention.

FIG. 2 shows a detailed schematic of the test facility 100 with the test article(s) in the test section 105 loaded such that they are parallel to the flow. FIG. 4 shows a similar schematic of the test facility 100 where the test article(s) are loaded perpendicular to the flow. The test article(s) can be oriented at any angle to the flow. Upon diffusion out of the test section 105, the flow proceeds to the exhaust heat recovery unit 106 and is then cooled further, regulated down to near ambient pressure and released to the environment through a silencer 107.

In other embodiments of the present invention, the flow exiting the test section 105 may first be expanded in a power turbine to reduce the discharge pressure and temperature into the heat recovery unit 106 as well as to reduce the electrical power requirement of the facility 100. This is especially true in the case of high speed centrifugal air compressors which should prove more compatible than reciprocating compressors for accepting the high speed shaft power from such a turbine. For such configurations, it is also possible to yield a net power production from the facility, or to create a power match between the compressors and turbine such that no net power is required or produced from the facility, aside from starting and shutdown.

The above-described facility 100 is started in the following manner. The industrial air compressor 115 is started via the electric drive motor 110 and is brought to full test flowrate. In this condition, the compressor discharge pressure will be lower than testing pressure due to the low temperature at the choked throttle (i.e. test section 105). A fuel compressor is started via its drive motor and brought to full test pressure and the fuel is injected into the combustor 104 and ignited. At this point, the air compressor discharge pressure rapidly achieves full test pressure.

Once the facility 100 is operating, control is maintained as follows. The facility working fluid flow rate is controlled via the speed of the air compressor 115. The temperature of the test section 105 is controlled via fuel compressor speed and/or fuel control valves. The test section pressure then depends upon both the air compressor and the set test section temperature.

The facility 100 is shut down by first shutting down the fuel compressors, thereby shutting off the combustion in the combustion section 104. The air compressor 115 remains on until the facility 100 is sufficiently cooled, and then it too is shut down. The safety features of this facility 100 may include containment of failed parts within the test section as well as containment of the test facility 100 within the test cell building, emergency fuel shutoff valves with atmospheric vents, and a fire extinguishing system for the facility.

The test facility 100 features operating costs far below those of engine testing, while providing a test environment similar to that of any existing or future gas turbine engine. Additionally, both steady-state and cyclic testing may be performed. The operating costs are a combination of fuel costs and electrical costs for operating the drive motors. The electrical costs may be further reduced via power purchase agreements with local utilities that may include operation during low-demand hours (such as at night) to provide low-cost electricity.

FIG. 2 is a longitudinal cross-sectional view of a first embodiment of a test section 200 incorporated into the test facility 100 of the present invention. FIG. 2 displays a test section housing 201 which includes both a combustor section 202 and a central test section 203. The combustor section 202 is therefore incorporated into the overall test section 200, and is included in the same housing 201 which includes the main central test section 203. Alternatively, the combustor section 202 may be separate from the central test section 203, and may not be included in a single integrated housing, but may be separable or removable from the central test section 203 housing. The test section 201 is substantially axisymmetric about a central longitudinal axis 204, such that many chambers and passages defined therein are annular or bodies of revolution about the central axis 204.

The test section housing 201 defines multiple flow paths, including a first flow path 205, and a second flow path 210, each flow path having upstream and downstream ends, respectively, which flow directions are indicated by the arrows in FIG. 2. The first flow path 205 generally corresponds to the non-reacting "cold" flow within the test section 200, while the second flow path 210 generally corresponds to the combusting "hot" flow within the test section 200. Arrows 211, 212, 213, 214, 215, 216, and 217 correspond to the cold flow within the first flow path 205. Arrows 221, 222, 223, 224, and 225 correspond to the hot flow within the second flow path 210. The first flow path 205 is defined by inlet channels or holes 231, which receive the compressed air from the compressor 115. The air at this stage is relatively cool when compared with the flow elsewhere in the test section 200, but may still exceed 1000 degrees F. in temperature. The compressed air flows through inlet channels 231 along arrows 211 into an annular inlet chamber 232. The air is then directed in the direction of arrows 212 through radial orifices (not shown) on a central inner conduit 235, which is disposed in the test section housing 201 and centered substantially about the central axis 204 as shown. The cooler, compressed air then flows through the conduit 235 along arrows 213, 214, 215, and 216, in a leftwards direction as shown in FIG. 2.

The conduit 235 is coupled to radial conduits 238 which direct the air flow from the conduit 235 radially outwards to the inlet of the annular combustion chamber 240. The first flow path 205 effectively ends at the junction of the radial conduits 238 with the combustion chamber 240, where incoming air is now mixed with fuel injected from one or more fuel injectors 242. The combustion chamber 240 effectively defines the beginning, or upstream portion, of the second flow path 210 through the test section housing 201. The combusting air and fuel mixture flows through the annular combustor section 202 along arrows 221 and 222 before entering an annular portion of the second flow path 210 between the inner conduit 235 and an outer sleeve 250 concentric about the conduit 235. The hot combusting fluid flows along arrows 223 as indicated in FIG. 2 before exiting the sleeve 250 and entering an annular exit chamber 255 along arrows 224 as shown. The second flow path 210 through the test section 200 thereby effectively terminates as the flow exits the exit chamber 255 through an exit conduit 260 along arrow 225 as shown.

The portion of the second flow path 210 between the inner conduit 235 and sleeve 250 is a region of very high temperature and pressure, as well as considerable flow velocity. While temperatures may range as high as 4000 to 4500 degrees F., at pressures of up to 50 atm, the local flow Mach number may be as high as 0.8: subsonic, but approaching the transonic range. These conditions effectively simulate the conditions in a real engine, and allow for test materials to be subjected to severe thermal, fluid dynamic, and mechanical stresses. A borescope 265 may also be provided to allow for observation of test materials deposited on the outer surface of the inner conduit 235.

The present invention therefore provides a relatively low-cost, efficient means for testing a material under the severe loads of a real engine, without having to use a real engine or its components. In particular, the invention provides a steep temperature gradient through the wall of the inner conduit 235. The gradient is created between: (i) the flow of hot combusting gases through a portion of the second flow path 210 between the inner conduit 235 and the outer sleeve 250, and (ii) the flow of relatively cool source air through the portion of the first flow path 205 inside the inner conduit pipe 235. The two flows may be counter flows as shown in FIG. 2. Alternatively, the first flow path 205 may be rearranged to be aligned in the same direction as the hot flow around the inner conduit 235. In either case, the resultant convective cooling creates a sharp temperature gradient that provides a simulation of engine conditions previously unavailable in known test rigs. By way of non-limiting example, the temperature gradients achieved may be in the range of between 250 and 1000 degrees F. across a test material coating 0.020 inches thick. In addition, film cooling may be locally achieved over the surface inner conduit pipe 235 by providing holes or orifices therein.

Figure 3:
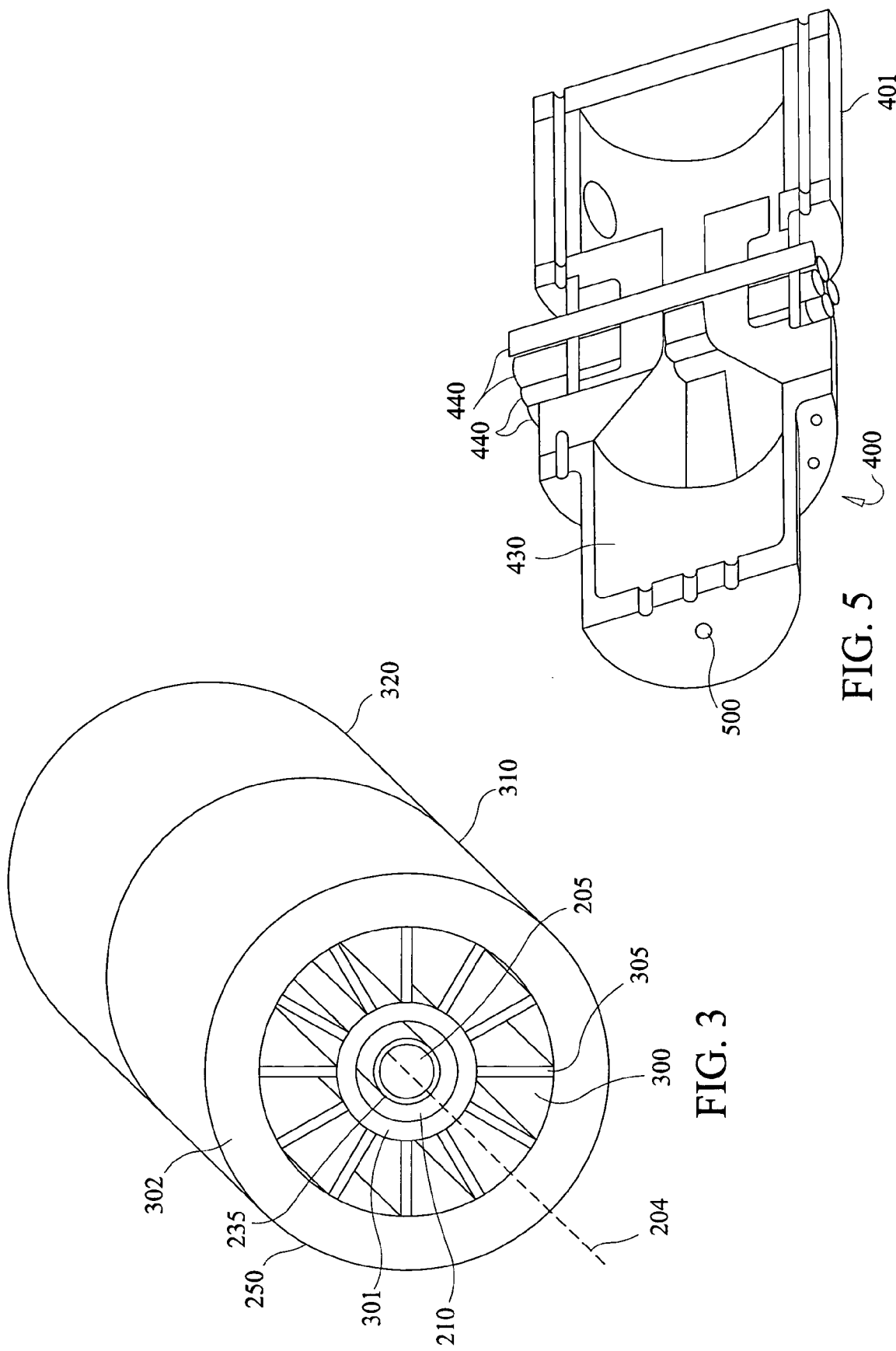
FIG. 3 is a perspective view of a section of the test pipe and cooling sleeve incorporated into the test section of FIG. 2.

FIG. 3 is a perspective view of a particular embodiment of a section of the inner conduit test pipe 235 and outer cooling sleeve 250 incorporated into the test section 200 of FIG. 2. In this embodiment, the outer sleeve 250 includes a number of axial cooling channels 300 which run parallel to the central axis 204 about which the conduit 235 and sleeve 250 are centered. The cooling channels 300 are defined by radial sections created between an inner pipe 301 and an outer pipe 302 of the sleeve 250, the sections being subdivided by a number of spars 305 between the two pipes 301 and 302. Cooling channels can also be arranged to allow coolant to flow circumferentially around the housing. A coolant, such as water, or some other suitable coolant, is pumped into the cooling sleeve 250 into the plurality of cooling channels 300 to cool the inner pipe 301, which is in contact with the hot combusting flow in the second flow path 210 through the test section. The cooler fluid first flow path 205 is also shown circumscribed by the section of inner conduit 205.

Both the inner conduit 235 and the outer sleeve 250 may be axially sectioned into interlocking attachable and detachable axial sections, such as sleeve sections 310 and 320 shown in FIG. 3. Each axial section may be fitted with complementary male and female thread portions on opposite axial sides of each section of the inner conduit 235 and sleeve 250. The inner conduit 235 may therefore include a plurality of serially connected longitudinal pipe sections. The sleeve 250 itself may have such interlocking threads on each of its inner and outer pipes 301 and 302, respectively. In this manner, the overall length and dimensions of the test section apparatus can be scaled and adjusted to the needs of the user. Furthermore, differing test materials may be deposited or incorporated into different axial sections of the inner conduit 235, such that various test samples may be tested at the same time. The test samples may also be inlaid into the conduit 235 in the form of discrete surface sections or coupons, to allow for even more varied test material arrangements.

Examples of flow conditions in the test section are as follows. Inside the inner conduit 235 in the first flow path 205, the flow may be at a pressure as high as 50 atm, a temperature as high as 1100 degrees F., and a Mach number as high as 0.6. Inside the portion of the second flow path 210 between the inner conduit 235 and outer sleeve 250, the flow may be at a pressure as high as 50 atm, a temperature as high as 4500 degrees F., and a Mach number as high as 0.8. The cooling water flowing in channels 300 may be at significantly lower temperatures, such as 100 degrees F. These channels are designed to handle the radial pressure differential developed by the difference in pressure drop between the incompressible coolant and the compressible hot gas as they flow axially.

FIG. 4 is a longitudinal cross-sectional view of a second embodiment of a test section 400 incorporated into a test facility of the present invention, such as the overall test facility described in FIG. 1. In this embodiment, test section 400 includes a housing 401, which includes both a combustor section 402 and a central test section 403. As with the previous embodiment shown in FIG. 2, the combustor section 402 is therefore incorporated into the overall test section 400, and is included in the same housing 401 which includes the main central test section 403. Alternatively, the combustor section 402 may be separate from the central test section 403, and may not be included in a single integrated housing, but may be separable or removable from the central test section 403. The test section housing 401 is substantially axisymmetric about a central longitudinal axis 404; such that the chambers and passages defined therein may be annular bodies of revolution about the central axis 404.

The test section housing 401 defines multiple flow paths, including a first or primary flow path 405, and a second or secondary flow path 410, each flow path having upstream and downstream ends, respectively, which flow directions are indicated by the arrows in FIG. 4. The first flow path 405 generally corresponds to the combusting "hot" flow within the test section 400, while the second flow path 410 generally corresponds to the non-reacting "cold" flow within the test section 400. Arrows 411, 412, and 413 correspond to the hot flow within the first flow path 405. Arrows 421, 422, and 423 correspond to the cooler flow within the second flow path 410. Compressed air is supplied through inlet holes (not shown) along arrows 411 into the combustor chamber 430 in the upstream portion of the first flow path 405 defined by the housing 401. The supplied air is mixed with fuel from one or more fuel nozzles or injectors 435. The hot combusting fuel and air mixture then flows over a test article 440 disposed substantially perpendicular to the flow. The test article 440 could be disposed at any angle to the flow in the first flow path 405 by orienting the article 440 in the housing 401 in the desired manner.

A second flow path 410 is defined first by an inlet chamber 450 defined by the housing 401, into which compressed air is supplied along arrow 421. This cooler air, having conditions comparable to the cooler air supplied into the first flow path 205 of the test section 200 shown in FIG. 2, enters an inner channel 460 defined within the test article 440 and flows along arrow 422 as shown. The inner channel 460 terminates within the test article 440 at a longitudinal position downstream of the intersection of the test article 440 with the first flow path 405, whereby the air flowing within the test article 440 exits the article though holes (not shown) and flows along arrow 423 into an exit chamber 465. This exit chamber 465 can function as part of a plenum, whereby the air flow can be routed to the input of the combustor section 402 and ported into the combustor chamber 430. Another recirculation path may be provided by linking the downstream chamber 468 of the primary flow path 405 in the test section housing 401 with the inlet chamber 450 of the secondary flow path 410 through a channel 469 as shown.

The flow of hot combusting fluid in the first flow path 405 therefore flows around the test article 440 while cooler air flows within the article 440, to create a sharp temperature gradient through the walls of the test article 440, or through a test material that is deposited onto the outer surface of the test article 400. Alternatively, the test article 440 may have a test material portion embedded therein, incorporated into a portion of its walls, or mechanically attached. The article 440 may be of any shape or configuration, but is shown in FIG. 4 to be shaped like a rod, with circular or elliptical cross-section. The article 440 may also have an airfoil shaped cross-section. The article 440 may be loaded with a load cell or other suitable loading mechanism to place a mechanical stress on the article 440, such as a tensile load T as shown. The loads may be steady or transient, gradual or alternating, and may be used to mimic and simulate the conditions in a real engine. In this manner, the test section 400 may be used to subject test materials and test samples on the test article 440 to a variety of combined thermal, fluid dynamic and mechanical loads, so as to more accurately simulate the conditions in a real gas turbine engine.

FIG. 5 is a perspective view of a longitudinal cross-section of the test section 400 shown in FIG. 4. As shown in FIG. 5, the test section 400 housing 401 includes several inlet holes or channels for incoming compressed air to be supplied into the combustion chamber 430. A plurality of test articles may be arranged parallel to one another as shown; to increase the available area of test samples and specimens exposed to the flow conditions inside the test section 400.

The test facilities described herein include several other features of note. The first is a removable front plate 275 included in the embodiment shown in FIG. 2. The front plate 275 is disposed over a removal channel or port 278 through which a proximal end portion of the inner conduit pipe 235 is disposed. The entire length of the inner conduit pipe 235 may be slidably disposed in the test section 200 and through the removal port 278, such that when the front plate 275 is removed, the inner pipe 235 may be easily pulled out and repaired, refitted, or replaced as desired.

Another feature includes a seal and sealing mechanism present in both the embodiments disclosed in FIGS. 2 and 4. FIGS. 6A and 6B show alternate embodiments of a spring loaded compression seal incorporated into the present invention. FIG. 6A is an enlarged view of the seal mechanism 280 in the test section 200 shown in FIG. 2. The seal 280 seals the first flow path 205 between the inner conduit pipe 235 and the test section housing 201. The seal 280 includes a spring 600 and two piston rings 601 and 602, which are each circumscribed around the inner conduit pipe 235. Each piston ring 601 and 602 has an inner diameter that is slightly smaller than the outer diameter of the inner conduit pipe 235 so as to provide a compression seal between the two elements. Furthermore, the load from spring 600 in the directions L as shown provides a compression seal between the surface of the test section housing 201 contacting each of the seals 601 and 602. Therefore, fluid flowing into the conduit 235 along arrows F as shown is sealed into the first flow path 205 and cannot escape the test section housing 201.

A similar arrangement of a seal mechanism 480 in the embodiment of FIG. 4 is shown in FIG. 6B. The seal 480 also includes a spring 610 attached to piston rings 611 and 612, which each provide compression seals between the test article 440 and the housing 401, to seal high pressure flow flowing through the portion of the secondary flow path 410 along arrows F.

Both the test sections 201 and 401 in FIGS. 2 and 4, respectively, will require a fair degree of cooling, and may include several cooling circuits or channels 700 about the various passages and chambers therein, as shown. Examples of materials used in constructing the test section include various metals and/or alloys, including stainless steel, or copper for the sleeve 250. Examples of test materials include various thermal barrier coatings, including an air-plasma spray coating. TBC coatings may themselves also be used to line the surfaces of the flow paths within the test sections 201 and 401 to protect the sections.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A facility for testing a material, comprising:
a test section housing defining a first flow path and a second flow path, each flow path having upstream and downstream ends, respectively;
a combustor section defining a combustion chamber in fluid communication with the upstream end of the second flow path and the downstream end of the first flow path;
at least one fuel injector disposed proximate the downstream end of the first flow path and proximate the upstream end second flow path;
a conduit enclosing a portion of the first flow path for accommodation therethrough of a first fluid flow having a first temperature;
a sleeve concentric about the conduit to define an annular portion of the second flow path for accommodation therethrough of a second fluid flow having a temperature higher than the first temperature; and
a test material disposed on the conduit in contact with the annular portion.

2. The facility of claim 1, further comprising:
a source of compressed fluid coupled to the test section at the upstream end of the first flow path; and
an exhaust channel coupled to the downstream end of the second flow path.

3. The facility of claim 2, further comprising:
a heat exchanger disposed in the exhaust channel in thermal communication with the source of compressed fluid.

4. The facility of claim 2, further comprising:
an exhaust valve and silencer coupled to the exhaust channel.

5. The facility of claim 1,
wherein the first fluid flow is oriented along an axis in a first direction and the second fluid flow is oriented along the axis in a direction opposite the first direction.

6. The facility of claim 1,
wherein the sleeve defines a plurality of channels for accommodation therethrough of a fluid coolant.

7. The facility of claim 1,
wherein the conduit comprises a first plurality of serially connected longitudinal pipe sections.

* * * * *